United States Patent
Wahlstrand et al.

(10) Patent No.: US 8,478,402 B2
(45) Date of Patent: Jul. 2, 2013

(54) DETERMINING INTERCARDIAC IMPEDANCE

(75) Inventors: John D. Wahlstrand, Shoreview, MN (US); Timothy J. Denison, Minneapolis, MN (US); Wesley A. Santa, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 364 days.

(21) Appl. No.: 12/263,346

(22) Filed: Oct. 31, 2008

(65) Prior Publication Data
US 2010/0114223 A1 May 6, 2010

(51) Int. Cl.
*A61N 1/00* (2006.01)
(52) U.S. Cl.
USPC ............ 607/8; 607/7; 607/28; 600/547
(58) Field of Classification Search
USPC .................... 607/7, 8, 28; 600/547
See application file for complete search history.

(56) References Cited

U.S. PATENT DOCUMENTS

| | | |
|---|---|---|
| 1,342,885 A | 6/1920 | Armstrong |
| 3,130,373 A | 4/1964 | Braymer |
| 3,603,997 A | 9/1971 | Brouwer |
| 3,735,274 A | 5/1973 | Nelson |
| 3,780,725 A | 12/1973 | Goldberg |
| 4,138,649 A | 2/1979 | Schaffer |
| 4,177,819 A | 12/1979 | Kofsky et al. |
| 4,188,586 A | 2/1980 | Egami |
| 4,279,258 A | 7/1981 | John |
| 4,579,125 A | 4/1986 | Strobi et al. |
| 4,610,259 A | 9/1986 | Cohen et al. |
| 4,612,934 A | 9/1986 | Borkan |
| 4,733,667 A | 3/1988 | Olive et al. |
| 4,933,642 A | 6/1990 | Lee |
| 4,979,230 A | 12/1990 | Marz |
| 5,024,221 A | 6/1991 | Morgan |
| 5,061,593 A | 10/1991 | Yoerger et al. |
| 5,105,167 A | 4/1992 | Peczalski |

(Continued)

FOREIGN PATENT DOCUMENTS

| | | |
|---|---|---|
| CN | 101099670 A | 1/2008 |
| EP | 0354060 A2 | 2/1990 |

(Continued)

OTHER PUBLICATIONS

Min et al., "Electrical Impedance and Cardiac Monitoring—Technology, Potential and Applications", International Journal of Bioelectromagnetism, International Society for Bioelectromagnetism, vol. 5, No. 1, Jan. 2003, pp. 53-56.

(Continued)

*Primary Examiner* — Niketa Patel
*Assistant Examiner* — Mallika D Fairchild
(74) *Attorney, Agent, or Firm* — Michael C. Soldner (57) ABSTRACT

A system and method for determining complex intercardiac impedance to detect various cardiac functions are disclosed involving a signal generator means for providing an adjustable direct current signal, a modulator for modulating the adjustable direct current signal to produce a modulated signal, at least one electrode for propagating the modulated signal across a myocardium, at least one sensor for detecting an outputted modulated signal from the myocardium, and at least one circuit to reduce the influence of process noise (aggressors) in the outputted modulated signal. The at least one circuit comprises an amplifier, a demodulator, and an integrator. The amplitude and phase of the final outputted modulated signal indicate the complex impedance of the myocardium. Changes in the complex impedance patterns of the myocardium provide indication of reduced oxygen and blood flow to the myocardium. The apparatus can be employed in implantable devices, including cardiac pacemakers and implantable cardioverter defibrillators.

29 Claims, 9 Drawing Sheets

U.S. PATENT DOCUMENTS

| | | |
|---|---|---|
| 5,113,143 A | 5/1992 | Wei |
| 5,179,947 A | 1/1993 | Meyerson et al. |
| 5,205,285 A | 4/1993 | Baker, Jr. |
| 5,282,840 A | 2/1994 | Hudrlik |
| 5,311,876 A | 5/1994 | Olsen et al. |
| 5,334,222 A | 8/1994 | Salo et al. |
| 5,458,117 A | 10/1995 | Chamoun et al. |
| 5,477,481 A | 12/1995 | Kerth |
| 5,619,536 A | 4/1997 | Gourgue |
| 5,663,680 A | 9/1997 | Nordeng |
| 5,725,558 A | 3/1998 | Warnke |
| 5,777,235 A | 7/1998 | Altwein |
| 5,782,884 A | 7/1998 | Stotts et al. |
| 5,843,139 A | 12/1998 | Goedeke et al. |
| 5,928,272 A | 7/1999 | Adkins et al. |
| 6,011,990 A | 1/2000 | Schultz et al. |
| 6,016,444 A | 1/2000 | John |
| 6,061,593 A | 5/2000 | Fischell et al. |
| 6,064,257 A | 5/2000 | Sauer |
| 6,066,163 A | 5/2000 | John |
| 6,070,101 A | 5/2000 | Struble et al. |
| 6,129,681 A | 10/2000 | Kuroda et al. |
| 6,130,578 A | 10/2000 | Tang |
| 6,161,042 A * | 12/2000 | Hartley et al. .................. 607/20 |
| 6,262,626 B1 | 7/2001 | Bakker et al. |
| 6,287,263 B1 | 9/2001 | Briskin |
| 6,360,123 B1 | 3/2002 | Kimchi et al. |
| 6,456,159 B1 | 9/2002 | Brewer |
| 6,463,328 B1 | 10/2002 | John |
| 6,522,914 B1 | 2/2003 | Huvelle et al. |
| 6,539,261 B2 | 3/2003 | Dal Molin |
| 6,584,351 B1 | 6/2003 | Ekwall |
| 6,617,838 B1 | 9/2003 | Miranda et al. |
| 6,621,334 B2 | 9/2003 | Ausserlechner |
| 6,625,436 B1 | 9/2003 | Tolson et al. |
| 6,667,760 B1 | 12/2003 | Limberg |
| 6,674,322 B2 | 1/2004 | Motz |
| 6,725,091 B2 | 4/2004 | Dal Molin |
| 6,754,535 B2 * | 6/2004 | Noren et al. .................. 607/28 |
| 6,810,285 B2 | 10/2004 | Pless et al. |
| 6,876,842 B2 | 4/2005 | Davie |
| 6,904,321 B1 | 6/2005 | Bornzin et al. |
| 6,993,380 B1 | 1/2006 | Modarres |
| 7,006,872 B2 | 2/2006 | Gielen et al. |
| 7,010,347 B2 | 3/2006 | Schecter |
| 7,038,532 B1 | 5/2006 | Bocko et al. |
| 7,098,823 B2 | 8/2006 | O'Dowd et al. |
| 7,146,208 B2 | 12/2006 | Holmstrom et al. |
| 7,146,218 B2 | 12/2006 | Esteller et al. |
| 7,171,258 B2 | 1/2007 | Goode |
| 7,233,198 B2 | 6/2007 | Niederkorn |
| 7,239,927 B2 | 7/2007 | Ganion |
| 7,295,061 B1 | 11/2007 | Dasgupta |
| 7,336,123 B2 | 2/2008 | Yoshida et al. |
| 7,376,463 B2 | 5/2008 | Salo et al. |
| 7,385,443 B1 | 6/2008 | Denison |
| 7,391,257 B1 * | 6/2008 | Denison et al. .................. 330/9 |
| 7,595,648 B2 | 9/2009 | Ungaretti et al. |
| 7,622,988 B2 | 11/2009 | Denison et al. |
| 7,671,672 B2 | 3/2010 | McConnell |
| 7,847,628 B2 | 12/2010 | Denison |
| 2002/0091332 A1 | 7/2002 | Bombardini |
| 2003/0146786 A1 | 8/2003 | Gulati et al. |
| 2004/0077967 A1 | 4/2004 | Jordan |
| 2004/0077987 A1 | 4/2004 | Rapacki et al. |
| 2004/0141558 A1 | 7/2004 | Plisch et al. |
| 2005/0007091 A1 | 1/2005 | Makeig et al. |
| 2005/0081847 A1 | 4/2005 | Lee et al. |
| 2005/0118968 A1 | 6/2005 | Cowley |
| 2005/0182447 A1 | 8/2005 | Schecter |
| 2005/0282517 A1 | 12/2005 | Cowley |
| 2006/0055456 A1 | 3/2006 | Niederkorn |
| 2006/0116591 A1 | 6/2006 | Cooper |
| 2006/0133550 A1 | 6/2006 | Bolton et al. |
| 2006/0135877 A1 | 6/2006 | Giftakis et al. |
| 2006/0139192 A1 | 6/2006 | Morrow et al. |
| 2006/0139193 A1 | 6/2006 | Morrow et al. |
| 2006/0173501 A1 | 8/2006 | Stickney et al. |
| 2006/0184060 A1 | 8/2006 | Belalcazar et al. |
| 2006/0241357 A1 | 10/2006 | Chirife |
| 2006/0281427 A1 | 12/2006 | Isaac et al. |
| 2006/0293720 A1 | 12/2006 | DiLorenzo |
| 2007/0010755 A1 | 1/2007 | Sarkela et al. |
| 2007/0016095 A1 | 1/2007 | Low et al. |
| 2007/0032737 A1 | 2/2007 | Causevic et al. |
| 2007/0077907 A1 | 4/2007 | Rector |
| 2007/0216477 A1 | 9/2007 | McConnell |
| 2007/0249953 A1 | 10/2007 | Frei et al. |
| 2008/0015659 A1 * | 1/2008 | Zhang et al. .................. 607/62 |
| 2008/0180278 A1 | 7/2008 | Denison |
| 2008/0269630 A1 | 10/2008 | Denison et al. |
| 2008/0269631 A1 | 10/2008 | Denison et al. |
| 2008/0269841 A1 | 10/2008 | Grevious et al. |
| 2009/0082691 A1 | 3/2009 | Denison et al. |
| 2010/0033240 A1 | 2/2010 | Denison et al. |
| 2010/0113964 A1 | 5/2010 | Wahlstrand et al. |
| 2010/0324442 A1 | 12/2010 | Blomqvist |
| 2010/0327887 A1 | 12/2010 | Denison et al. |
| 2011/0068861 A1 | 3/2011 | Denison |

FOREIGN PATENT DOCUMENTS

| | | |
|---|---|---|
| EP | 0568197 | 3/1993 |
| EP | 0789449 A2 | 8/1997 |
| GB | 1249395 | 10/1971 |
| JP | 4717841 | 9/1972 |
| JP | 5615112 | 2/1981 |
| JP | 6224659 | 8/1994 |
| JP | 7120207 | 5/1995 |
| JP | 10504099 | 4/1998 |
| JP | 2006279377 | 10/2006 |
| WO | WO 97/10747 A1 | 3/1997 |
| WO | WO 02/01711 A1 | 1/2002 |
| WO | WO 02/03087 A1 | 1/2002 |
| WO | WO 2006/066098 A1 | 6/2006 |
| WO | WO 2006/126186 A2 | 11/2006 |
| WO | WO 2008103078 A1 * | 8/2008 |
| WO | WO2008/105692 A1 * | 9/2008 |
| WO | WO 2008/105692 A1 | 9/2008 |
| WO | 2009042172 | 4/2009 |
| WO | 2009042313 | 4/2009 |

OTHER PUBLICATIONS

Dzwonczk et al., "Myocardial Electrical Impedance Responds to Ischemia and Reperfusion in Humans", IEEE Transactions on Biomedical Engineering, IEEE Service Center, vol. 51, No. 12, Dec. 2004, pp. 2206-2209.

Kun et al., "Algorithm for Tissue Ischemia Estimation Based on Electrical Impedance Spectroscopy", IEEE Transactions on Biomedical Engineering, IEEE Service Center, vol. 50, No. 12, Dec. 2003, pp. 1352-1359.

(PCT/US2009/058127) PCT Notification of Transmittal of the International Search Report and the Written Opinion of the International Searching Authority, 14 pages.

Heinks, "Declaration Under 37 C.F.R. 1.132," dated Feb. 18, 2010, 5 pp.

Heinks, "Declaration Under 37 C.F.R. 1.132," dated May 26, 2009, 4 pp.

Martins et al., "A CMOS IC for Portable EEG Acquisition Systems," IEEE Transactions on Instrumentation and Measurement, vol. 47, No. 5, pp. 1191-1196, Oct. 1998.

Boser, "Capacitive Interfaces for Monolithic Integrated Sensors," Chapter in "RF Analog-to-Digital Converters; Sensor and Actuator Interfaces; Low-Noise Oscillators, PLLs and Synthesizers," R.J. van de Plaasche, J.H. Huijsing, and W.M.C. Sansen (eds.), Kluwer Academic Publishers, Nov. 1997.

Bakker et al., "A CMOS Nested-Chopper Instrumentation Amplifier with 100-nV Offset," IEEE Journal of Solid-State Circuits, vol. 35, No. 12, pp. 1877-1883, Dec. 2000.

Harrison et al., "Local Field Potential Measurement with Low-Power Analog Integrated Circuit," Engineering in Medicine and Biology Society, 2004, IEMBS '04, 26th Annual International Conference of the IEEE, vol. 2, pp. 4067-4070 vol. 6, Sep. 1-5, 2004.

Sanduleanu et al., "A Low Noise, Low Residual Offset, Chopped Amplifier for Mixed Level Applications," IEEE, 0-7803-5008-1/98, pp. 333-336, Sep. 1998.
Hadiashar et al., "A Chopper Stabilized CMOS Analog Multiplier with Ultra Low DC Offsets," Solid-State Circuits Conference, pp. 364-367, Sep. 2006.
Ying, "Chopper Stabilized Amplifiers," Term Paper, Department of Electrical and Computer Engineering, University of Toronto, 17 pp., Nov. 12, 2001.
Enz et al., "Circuit Techniques for Reducing the Effects of Opamp Imperfections," Proc. of the IEEE, vol. 84, No. 11, pp. 1584-1614, Nov. 1996.
Yazicioglu et al., "A 60uW 60nV/rtHz Readout Front-End for Portable Biopotential Acquisition Systems," ISSCC Digest of Technical Papers 2006, paper 2.6, Feb. 2006.
Makinwa, "Dynamic Offset Cancellation Techniques," Smart Sensor Systems '02, May 2002.
Ng et al., "A CMOS Analog Front-End IC for Portable EEG/ECG Monitoring Applications," IEEE Trans. on Circuits and Systems, vol. 52, No. 11, Nov. 2005.
Burt et al., "A Micropower Chopper-Stabilized Operational Amplifier using an SC Notch Filter with Synchronous Integration inside the Continuous-Time Signal Path," ISSCC Digest of Technical Papers 2006, paper 19.6, Feb. 2006.
Harrison et al., "A Low-Power Low-Noise CMOS Amplifier for Neural Recording Applications," IEEE J. of Solid-State Circuits, vol. 38, No. 6, pp. 958-965, Jun. 2003.
Wu et al., "A 1V 2.3mW Biomedical Signal Acquisition IC," ISSCC Digest of Technical Papers 2006, paper 2.7, Feb. 2006.
Harrison et al., "A Low-Power Integrated Circuit for a Wireless 100-Electrode Neural Recording System," ISSCC Digest of Technical Papers 2006, paper 30.2, Feb. 2006.
Avestruz et al., "A 5 µW/Channel Spectral Analysis IC for Chronic Bidirectional Brain-Machine Interfaces," IEEE Journal of Solid-State Circuits, vol. 43, No. 12, Dec. 2008, 19 pp.
Denison et al., "A 2.21µW 94nV/√Hz, Chopper-Stabilized Instrumentation Amplifier for EEG Detection in Chronic Implants" JSSC, vol. 42, No. 12, pp. 2934-2945, Dec. 2007.
Sarpeshkar, "Borrowing from biology makes for low-power computing," IEEE Spectrum, pp. 24-29, May 2006.
Denison et al., "An 8µW heterodyning chopper amplifier for direct extraction of 2µVrms Neuronal Brain Biomarkers," ISSCC, Jul. 2008, paper 8.1, 3 pp.
Anderson et al., "Recording Advances for Neural Prosthetics," in Engineering in Medicine and Biology Society, Sep. 2004. IEMBS 2004, 26th Annual International Conference of the IEEE, pp. 5352-5355, vol. 7.
Anderson et al., "Selecting the signals for a brain-machine interface," Curr Opin Neurobiol, vol. 14, pp. 720-726, Dec. 2004.
Denison et al., "A 2µW 100 nV/rtHz Chopper-Stabilized Instrumentation Amplifier for Chronic Measurement of Neural Field Potentials," Solid-state circuits, IEEE Journal, vol. 42, pp. 2934-2945, Dec. 2007.
Smart et al., "Automatic Detection of High Frequency Epileptiform Oscillations from Intracranial EEG Recordings of Patients with Neocortical Epilepsy," in Technical, Professional and Student Development Workshop, 2005 IEEE Region 5 and IEEE Denver Section, Apr. 2005, pp. 53-58.
Krusienski et al., "A µ-Rhythm Matched Filter for Continuous Control of a Brain-Computer Interface," Biomedical Engineering, IEEE Transactions on, vol. 54, Feb. 2007, pp. 273-280.
Harrison et al., "A Low-Power Integrated Circuit for a Wireless 100—Electrode Neural Recording System," Solid state circuits. IEEE Journal of, vol. 42, Jan. 2007, pp. 123-133.
Haddad et al., "An ultra low-power dynamic translinear cardiac sense amplifier for pacemakers," Circuits and Systems, Mar. 2003, vol. 5, pp. V37-V40.
Haddad et al., "Analog wavelet transform employing dynamic translinear circuits for cardiac signal characterization," Circuits and Systems, 2003, vol. 1, pp. 1-121-1-124.
Sarpeshkar et al., "An ultra-low-power programmable analog bionic ear processor," Biomedical Engineering, IEEE Transactions, vol. 52, Apr. 2005, pp. 711-727.

Sarpeshkar et al., "Low power circuits for brain—machine interfaces," Circuits and Systems, Sep. 2007, pp. 2068-2071.
Denison et al., "A 2.2µW 94nV/√Hz, Chopper-Stabilized Instrumentation Amplifier for EEG Detection in Chronic Implants," Solid-State Circuits Conference, 2007, Digest of Technical Papers, IEEE International, 3 pp.
Yazicioglu et al., "A 200µW Eight-Channel Acquisition ASIC for Ambulatory EEG Systems," Solid-State Circuits Conference, Jul. 2008, 3 pp.
Denison et al., "An 8µW Heterodyning Chopper Amplifier for Direct Extraction of 2µ, Vrms Neuronal Biomarkers," Solid-State Circuits Conference, Jul. 2008 Digest of Technical Papers, IEEE International, 3 pp.
Bakker et al., "A CMOS nested chopper instrumentation amplifier with 100nV offset," in Solid-State Circuits Conference, Feb. 2000, Digest of Technical Papers, IEEE International, pp. 156-157.
Makinaw et al., "A CMOS Temperature-to-frequency converter with an Inaccuracy of less than ±0.5° C. (3σ) from -40° C. to 105° C.," IEEE Journal of Solid State Circuits, vol. 41, No. 12, Dec. 2006, pp. 2992-2997.
Lee et al., "A 64 Channel Programmable Closed-Loop Deep Brain Stimulator with 8 channel Neural Amplifier and Logarithmic ADC," 2008 Symposium on VLSI Circuits Digest of Technical Papers, Mar. 2008, pp. 76-77.
Salthouse et al., "A practical micropower programmable bandpass filter for use in bionic ears," Solid-State Circuits, IEEE Journal, vol. 38, Jan. 2003, pp. 63-70.
Wattanapanitch et al., "An energy-efficient micropower neural recording amplifier," Biomedical Circuits and Systems, IEEE Transactions, vol. 1, No. 2, Jun. 2007, pp. 136-147.
Office Action for U.S. Appl. No. 12/263,358, dated Feb. 25, 2011, 14 pages.
Response to Office Action dated Feb. 25, 2011, for U.S. Appl. No. 12/263,358, filed May 25, 2011, 5 pp.
Liu, "Operational amplifiers," in: Demystifying Switched Capacitor Circuits (Demystifying Technology, vol. 1), May 11, 2006, pp. 15-26.
Moualla et al., "Chopped Folded Cascode Bulk Driven OTA", Proceedings of the International Interdisciplinary Honeywell EMI 2005, May 26, 2005, pp. 185-189.
Masui, "A 0.6 V Supply CMOS Amplifier Using Noise Reduction Technique of Autozeroing and Chopper Stabilization," 21st Century COE Program, Hiroshima University, Proceedings of the Fifth Hiroshima International Workshop, Jan. 29-30, 2007, 5 pp.
Bakker, "High-Accuracy CMOS Smart Temperature Sensors," Thesis Delft University of Technology, Apr. 17, 2000, pp. 20, 21, 51 and 52.
Rajan et al., "Offset cancellation and 1/f noise suppression scheme for chopper amplifiers," IEEE, 2000, pp. 68-71.
Abidi, "CMOS wireless transceivers: the new wave," IEEE Communications Magazine 37, 119-124 (1999).
Rauscher, "Practical Realization of an Analyzer Operating on the Heterodyne Principle," Chapter 4 (partial) of Fundamentals of Spectrum Analysis (Rohde & Schwarz, 2001 ). pp. 34-64. With 2 pages of front matter and 2 pages of diagrams.
Sarpeshkar et al., "Low power circuits for brain—machine interfaces," IEEE Transactions on Biomedical Circuits and Systems, Sep. 2008, vol. 2, No. 3, pp. 173-183.
Yates, "An ultra low power low noise chopper amplifier for wireless EEG". In 49th IEEE International Midwest Symposium on Circuits and Systems, 2006. MWSCAS '06., vol. 2, 449-452 (IEEE, 2006).
Office Action from U.S. Appl. No. 12/263,358, dated Aug. 8, 2011, 16 pages.
International Preliminary Report on Patentability from corresponding PCT Application Serial No. PCT/US2009/058127 dated May 3, 2011 (8 pages).
Japanese Office Action from Japanese application No. 2009-548232, dated Apr. 20, 2011, 4 pp. (citing JP 565112 and JP 4717841).
Japanese Office Action from Japanese application No. 2009-548231, dated May 18, 2011, 2 pp. (citing JP 4717841).

* cited by examiner

DETERMINING INTERCARDIAC IMPEDANCE

BACKGROUND OF THE DISCLOSURE

The present disclosure relates to determining intercardiac impedance. In particular, it relates to determining complex intercardiac impedance to detect various cardiac functions.

SUMMARY OF THE DISCLOSURE

The present disclosure relates to an apparatus, system, and method for determining intercardiac impedance to detect various cardiac functions. In one or more embodiments, the method for determining complex intercardiac impedance involves providing an adjustable direct current signal, modulating the adjustable direct current signal to produce a modulated signal, propagating the modulated signal across a myocardium, detecting an outputted modulated signal from the myocardium, and using at least one circuit to reduce the influence of process noise (aggressors) in the outputted modulated signal.

In one or more embodiments, the at least one circuit performs the steps comprising amplifying the outputted modulated signal to produce a second outputted modulated signal, wherein the second outputted modulated signal has a signal of interest that is amplified at a higher frequency than the process noise (aggressors); demodulating the second outputted modulated signal to produce a third outputted modulated signal, wherein the third outputted modulated signal has the signal of interest demodulated to a lower frequency and the process noise (aggressors) becomes modulated to a higher frequency; and passing the third outputted modulated signal through an integrator to produce a fourth outputted modulated signal, wherein the fourth outputted modulated signal has the signal of interest retained and the process noise (aggressors) filtered out.

In one or more embodiments, the amplitude and phase of the fourth outputted modulated signal indicate the complex impedance of the myocardium. In addition, changes in the complex impedance patterns of the myocardium provide indication of various cardiac functions and an ischemic event. Also, changes in patterns sensed by a combination of correlated sensors for specific regions of the heart provide indication of various cardiac functions and an ischemic event.

In one or more embodiments, the direct current signal is adjustable. Additionally, in some embodiments, the modulated signal has a nominal frequency of approximately 4 kilohertz to prevent interference with functions of other implanted devices.

In one or more embodiments, the method for determining intercardiac impedance may further comprise the steps of generating a signal when an ischemic event is indicated, where the signal contains an alert message; and transmitting the signal.

In one or more embodiments, the apparatus, system, and/or method is employed with at least one implantable medical device (IMD). In some embodiments, the at least one implantable medical device (IMD) is a cardiac pacemaker. In other embodiments, the at least one implantable medical device (IMD) is an implantable cardioverter defibrillator (ICD).

In one or more embodiments, a system is used for determining intercardiac impedance. The system comprises a signal generator for providing an adjustable direct current signal, a modulator for modulating the adjustable direct current signal to produce a modulated signal, at least one electrode for propagating the modulated signal across a myocardium, at least one sensor for detecting an outputted modulated signal from the myocardium; and at least one circuit to reduce the influence of process noise (aggressors) in the outputted modulated signal.

In one or more embodiments, at least one circuit comprises an amplifier for amplifying the outputted modulated signal to produce a second outputted modulated signal, wherein the second outputted modulated signal has a signal of interest that is amplified at a higher frequency than the process noise (aggressors); a demodulator for demodulating the second outputted modulated signal to produce a third outputted modulated signal, wherein the third outputted modulated signal has the signal of interest demodulated to a lower frequency and the process noise (aggressors) becomes modulated to a higher frequency; and an integrator for passing the third outputted modulated signal through to produce a fourth outputted modulated signal, wherein the fourth outputted modulated signal has the signal of interest retained and the process noise (aggressors) filtered out, wherein the amplitude and phase of the fourth outputted modulated signal indicate the complex impedance of the myocardium.

In one or more embodiments, at least one electrode is a left ventricular tip (LVTIP) electrode, and the at least one sensor is a right ventricular coil (RVCOIL) sensor. In some embodiments, the at least one electrode is a left ventricular tip (LVTIP) electrode, and the at least one sensor is a right ventricular ring (RVRING) sensor. In other embodiments, the at least one electrode is a right ventricular tip (RVTIP) electrode, and the at least one sensor is a right ventricular ring (RVRING) sensor. In some embodiments, the at least one electrode is a left ventricular tip (LVTIP) electrode, and the at least one sensor is a left superior vena cava coil (SVCCOIL) sensor. In other embodiments, the at least one electrode is a right ventricular tip (RVTIP) electrode, and the at least one sensor is a superior vena cava coil (SVCCOIL) sensor.

In one or more embodiments, the system for determining intercardiac impedance may further comprise a signal generator for generating a signal when an ischemic event is indicated, where the signal contains an alert message; and a transmitter for transmitting the signal.

In one or more embodiments, a system is used for determining intercardiac impedance. The system comprises a signal generator means for providing an adjustable direct current signal; a modulator means for modulating the adjustable direct current signal to produce a modulated signal; at least one electrode means for propagating the modulated signal across a myocardium; at least one sensor means for detecting an outputted modulated signal from the myocardium; and at least one circuit means for reducing the influence of process noise (aggressors) in the outputted modulated signal.

In one or more embodiments, the at least one circuit means comprises an amplifier means for amplifying the outputted modulated signal to produce a second outputted modulated signal, wherein the second outputted modulated signal has a signal of interest that is amplified at a higher frequency than the process noise (aggressors); a demodulator means for demodulating the second outputted modulated signal to produce a third outputted modulated signal, wherein the third outputted modulated signal has the signal of interest demodulated to a lower frequency and the process noise (aggressors) becomes modulated to a higher frequency; and an integrator means for passing the third outputted modulated signal through to produce a fourth outputted modulated signal, wherein the fourth outputted modulated signal has the signal of interest retained and the process noise (aggressors) filtered out, wherein amplitude and phase of the fourth outputted modulated signal indicate the complex impedance of the myocardium.

In one or more embodiments, the system for determining intercardiac impedance may further comprise a signal generator means for generating a signal when an ischemic event is indicated, where the signal contains an alert message; and a transmitter means for transmitting the signal.

BRIEF DESCRIPTION OF THE DRAWINGS

These and other features, aspects, and advantages of the present disclosure will become better understood with regard to the following description, appended claims, and accompanying drawings where:

DETAILED DESCRIPTION

The methods and apparatus disclosed herein provide an operative system for determining intercardiac impedance. Specifically, this system allows for determining complex intercardiac impedance to detect various cardiac functions including, but not limited to, contractility, capture detection, atrium-ventricle optimization, right ventricular function, left ventricular function, cardiac output (stroke volume), and right to left ventricular synchronization. In addition, this system allows for the monitoring of complex intercardiac impedance for the detection of ischemia, which is related to myocardial tissue viability. Ischemia is an absolute or relative shortage of blood supply to an organ, which causes tissue damage because of the lack of oxygen and nutrients to the affected tissue.

The present disclosure describes a system comprising an implantable medical device (IMD) that includes an intercardiac impedance measurement circuit. Implantable medical devices (IMDs) are devices that are designed to be implanted into a patient. Examples of implantable medical devices to be utilized with this system include, but are not limited to, cardiac pacemakers, implantable cardioverter defibrillators (ICDs), and other devices that include a combination of pacing and defibrillation including cardiac resynchronization therapy. These implantable devices are typically used to treat patients using electrical therapy. In addition, these devices may include electrical leads connected to sensors located on the myocardium that are used to monitor electrical signals.

The intercardiac impedance measurement circuit employed by this system is adapted to be coupled to implantable electrodes/sensors in order to obtain an intercardiac impedance signal between the electrodes/sensors. The amplitude and phase of the intercardiac impedance signal indicate the complex impedance of the myocardium. The complex impedance of the myocardium can be used to detect various cardiac functions.

The complex impedance of the myocardium typically fluctuates in a corresponding pattern with the beating of the heart. Changes in the complex impedance patterns of the myocardium can indicate reduced oxygen and blood flow to the myocardium and, thus, provide a method for an immediate indication of an acute ischemic event (acute myocardial infarction (AMI)). The system of the present disclosure monitors the impedance of the heart and, thus, is able to detect possible ischemia of the myocardium. In addition, changes in the patterns sensed by a combination of correlated sensors for specific regions of the heart may provide indication of various cardiac functions and/or an ischemic event. In the event that an ischemic event is detected, the system may cause a signal, which is carrying an alert message, to be generated and transmitted directly to the patient or sent through telemetry links to a monitoring receiver. Various telemetry methods and systems may be employed by the system of the present disclosure.

In the following description, numerous details are set forth in order to provide a more thorough description of the system. It will be apparent, however, to one skilled in the art, that the disclosed system may be practiced without these specific details. In the other instances, well known features have not been described in detail so as not to unnecessarily obscure the system.

Figure 1:
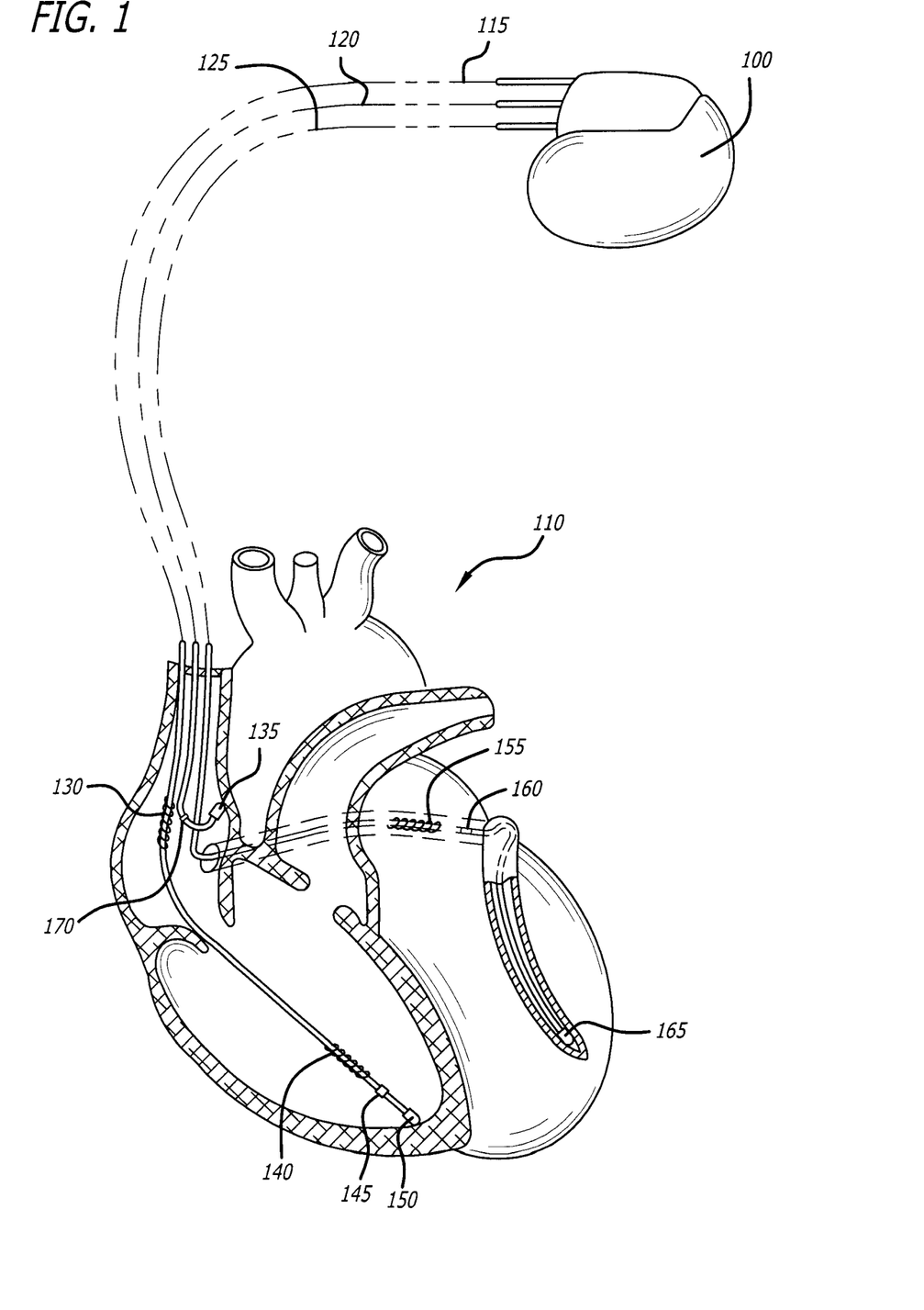
FIG. 1 is an illustration of a myocardium containing sensors for determining intercardiac impedance in accordance with at least one embodiment of the present disclosure.

FIG. 1 contains an illustration of a myocardium 110 containing electrodes and/or sensors for determining intercardiac impedance in accordance with at least one embodiment of the present disclosure. In this illustration, a human heart 110 is depicted as having electrodes and/or sensors (130, 135, 140, 145, 150, 155, 160, and 165) located at various points on the myocardium 110.

Also depicted in this figure is an implantable medical device (IMD) 100 that is in electrical communication with a patient's heart 110 by the use of at least three electrical leads (115, 120, and 125). Right ventricular lead 115 has at least a superior vena cava (SVC) coil electrode/sensor 130, a right ventricular coil (RVCOIL) electrode/sensor 140, a right ventricular ring (RVRING) electrode/sensor 145, and/or a right ventricular tip (RVTIP) electrode/sensor 150. In addition, right atrial lead 120 has at least a right atrial tip (RATIP) electrode/sensor 135 and/or a right atrial ring (RARING) electrode/sensor 170. Additionally, coronary sinus lead 125 has at least a left ventricular tip (LVTIP) electrode/sensor 165, multiple left ventricular (LV) electrodes/sensors (not shown in figure), a left atrial ring (LARING) electrode/sensor, and/or a left atrial coil (LACOIL) electrode/sensor.

In one or more embodiments, the system of the present disclosure is able to obtain an intercardiac impedance signal between at least one electrode and at least one sensor. In at least one embodiment, a right ventricle coil (RVCOIL) sensor 140 may detect an impedance signal that originated from left ventricle tip (LVTIP) electrode 165. In some embodiments, a right ventricular ring (RVRING) sensor 145 may detect an impedance signal that originated from the left ventricle tip (LVTIP) electrode 165. In one or more embodiments, a right ventricular ring (RVRING) sensor 145 may detect an impedance signal that originated from the right ventricular tip (RVTIP) electrode 150. These three specific signal paths each indicate an impedance signal that is proportional to blood flow, and provide a first derivative that is an indication of cardiac contractility. In addition, a change in complex impedance pattern for any of these particular signal paths can indicate that the portion of the heart the path crosses has been affected by ischemia. Thus, the various combinations of electrodes and sensors that are employed by this system provide comprehensive vector coverage of the heart.

In one or more embodiments, the disclosed system allows for determining intercardiac impedance to detect various cardiac functions including, but not limited to, contractility, capture detection, atrium-ventricle optimization, right ventricular function, left ventricular function, cardiac output (stroke volume), and right to left ventricular synchronization. A single impedance signal path can indicate various cardiac functions as well as the presence of ischemia of the corresponding region of the heart 110 that the signal path crosses.

In one or more embodiments, for example, an impedance signal path from a right ventricular tip (RVTIP) electrode 150 to a superior vena cava coil (SVCCOIL) sensor 130 can detect various cardiac functions of the right side of the heart 110. In another example, an impedance signal path from a right atrial tip (RATIP) electrode 135 to the superior vena cava coil (SVCCOIL) sensor 130 can also detect various cardiac functions of the right side of the myocardium 110. In an additional example, an impedance signal path from a left ventricular tip (LVTIP) electrode 165 to a superior vena cava coil (SVCCOIL) sensor 130 can detect various cardiac functions of the left side of the heart 110. In yet another example, an impedance signal patch from a right atrial ring (RARING) electrode 160 to a superior vena cava coil (SVCCOIL) sensor 130 can detect various cardiac functions of the left side of the heart 110.

In other embodiments of this system, the system may employ more or less electrodes and/or sensors than are illustrated in FIG. 1. Also, in alternative embodiments, electrodes and/or sensors may be placed at other locations of the myocardium 110 than are shown in the FIG. 1.

Figure 2:
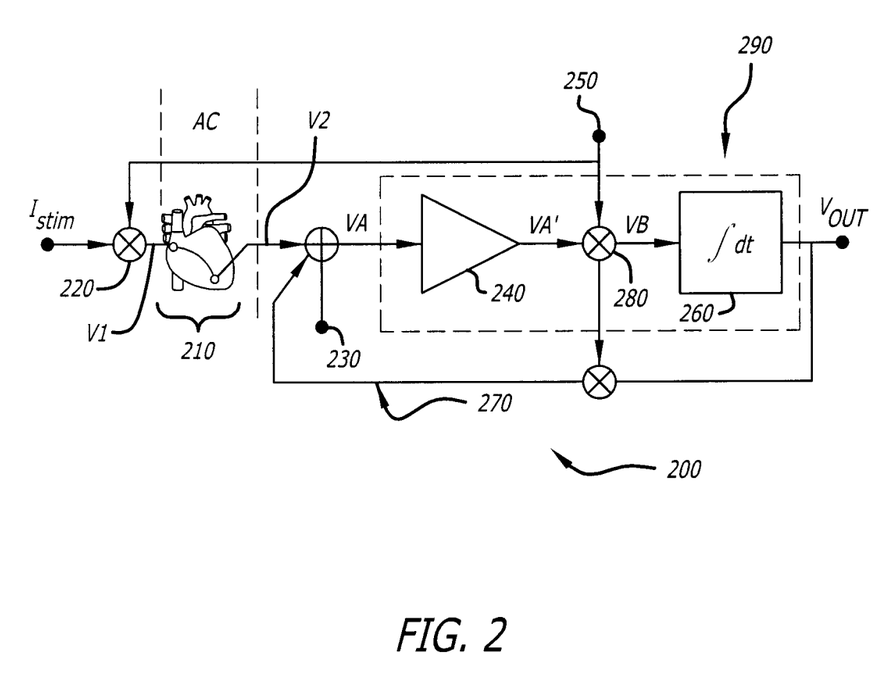
FIG. 2 is a schematic circuit diagram for determining intercardiac impedance in accordance with at least one embodiment of the present disclosure.

FIG. 2 contains a schematic circuit diagram 200 for determining intercardiac impedance in accordance with at least one embodiment of the present disclosure. In this figure, a stimulation current (Istim), which is a direct current (DC) signal, is first generated. The stimulation current (Istim) is adjustable. In one or more embodiments, the stimulation current (Istim) is adjustable at discrete values between approximately 500 nano amperes and approximately 10 micro amperes. In alternative embodiments, the stimulation current (Istim) may be adjustable at various other ranges. The current is generated by switching a programmable resistor in series with a supply. Alternatively, the stimulation current (Istim) may be generated by other means including, but not limited to, various signal generators.

The stimulation current (Istim) is then modulated 220 at a nominal frequency of approximately 4 kilohertz (KHz) by a modulator 250 to produce modulated signal V1. The nominal frequency of approximately 4 KHz prevents interference with functions of other implanted devices. The modulation of the stimulation current (Istim) allows for the stimulation and measurement circuitry to be isolated from the direct current (DC) potentials on the lead pathway. In alternative embodiments, the signal is modulated at various other frequencies. In one or more embodiments of this system, the signal is modulated into a square wave. However, in alternative embodiments, the signal can be modulated into, but not limited to, a sinusoid, or pulses.

The modulated signal V1 is then propagated from at least one electrode located on the myocardium through the myocardium 210. At least one sensor located on the myocardium 210 senses the outputted modulated signal V2. The outputted modulated signal V2 is combined with process noise (aggressors) 230. The resultant signal that contains the impedance signal of the heart with process noise (aggressors) 230 is outputted modulated signal VA. The resultant outputted modulated signal VA is then passed through at least one circuit 290 to reduce the influence of process noise (aggressors) 230 in the outputted modulated signal VA.

In the at least one circuit 290, the outputted modulated signal VA is amplified through an amplifier 240 to produce outputted modulated signal VA'. Outputted modulated signal VA' has a signal of interest that is amplified at a higher frequency than the process noise (aggressors) 230 within the signal. Outputted modulated signal VA' is then demodulated 280 by demodulator 250 to produce outputted modulated signal VB. Outputted modulated signal VB has a signal of interest that is demodulated to a lower frequency and its process noise (aggressors) 230 becomes modulated to a higher frequency.

In one or more embodiments, a feedback loop 270 is employed to reduce errors that result from the low bandwidth of the amplifier 240 and to set the gain. In the circuit, outputted modulated signal VB is passed through an integrator 260 to produce outputted modulated signal Vout. The integrator 260 stabilizes the feedback loop 270 and acts as a low pass filter. In one or more embodiments of the system, an additional resistor-capacitor (RC) low pass filter is included at the output of the at least one circuit 290 to further isolate the signal of interest.

The resultant signal of interest of the outputted modulated signal Vout indicates the impedance of the area of the myocardium that the signal passed through. If demodulator 250 is clocked in phase with the simulation current (Istim), the real impedance is measured from outputted modulated signal Vout. Alternatively, if the demodulator 250 is clocked at −90 degrees with respect to the stimulation current (Istim), the imaginary part of the impedance is measured from the outputted modulated signal Vout.

Figure 3:
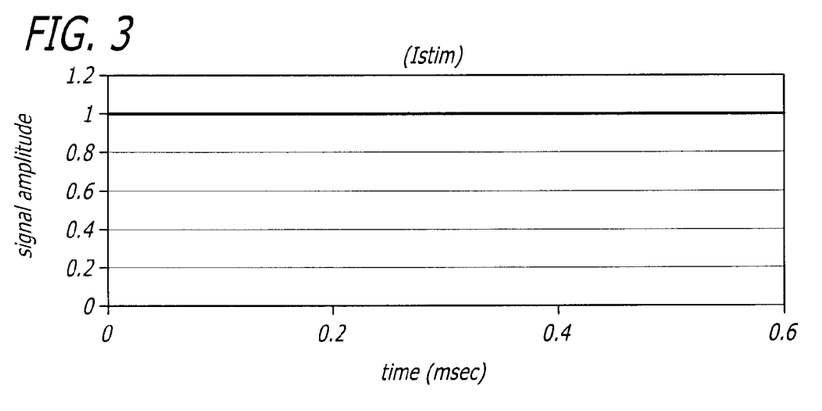
FIG. 3 is a graphical representation of the stimulation current (Istim) in the time domain in accordance with at least one embodiment of the present disclosure.
Figure 4:
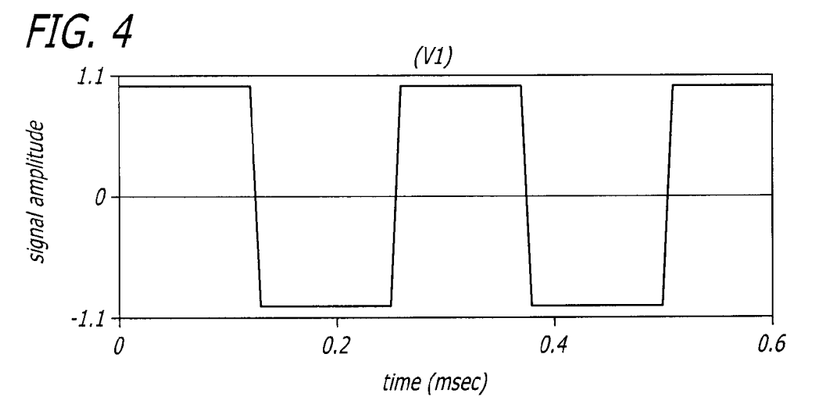
FIG. 4 is a graphical representation of modulated signal V1 in the time domain in accordance with at least one embodiment of the present disclosure.

FIG. 3 contains a graphical representation of the stimulation current (Istim) in the time domain in accordance with at least one embodiment of the present disclosure. In this figure, the stimulation current (Istim) is depicted as a direct current (DC) signal. FIG. 4 illustrates a graphical representation of modulated signal V1 in the time domain in accordance with at least one embodiment of the present disclosure. In this figure, the stimulation current (Istim) is shown to have been modulated at approximately 4 kHz into a square wave.

Figure 5:
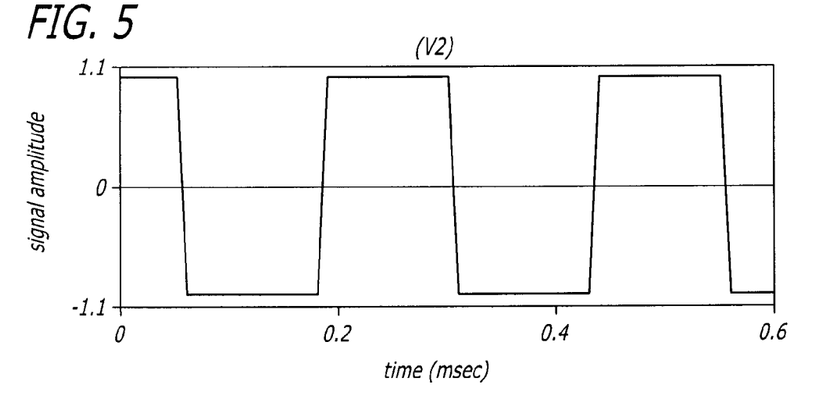
FIG. 5 is a graphical representation of outputted modulated signal V2 in the time domain in accordance with at least one embodiment of the present disclosure.

FIG. 5 illustrates a graphical representation of outputted modulated signal V2 in the time domain in accordance with at least one embodiment of the present disclosure. In this figure, the reactive outputted modulated signal V2 is depicted has having a shift in phase versus FIG. 4. The amount of shift in phase of the signal is related to the amount of the reactive component of the impedance of the signal.

Figure 6:
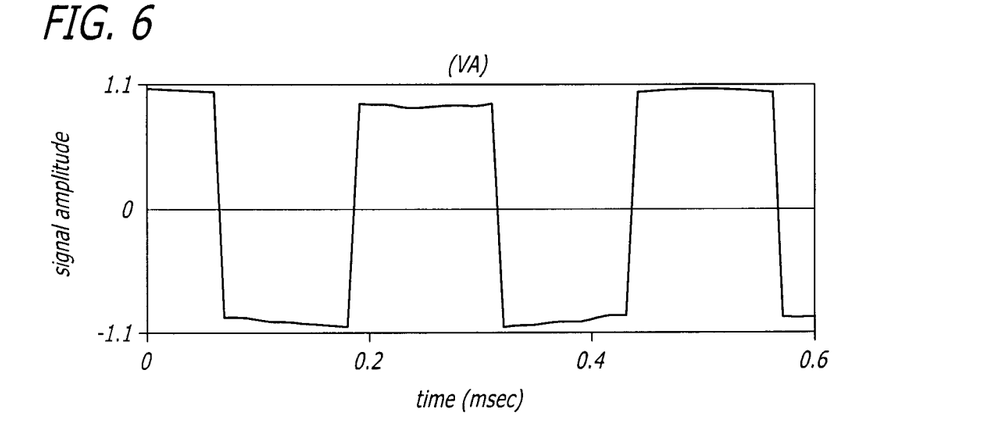
FIG. 6 is a graphical representation of outputted modulated signal VA in the time domain in accordance with at least one embodiment of the present disclosure.

FIG. 6 is a graphical representation of outputted modulated signal VA in the time domain in accordance with at least one embodiment of the present disclosure. In this figure, the outputted modulated signal VA includes process noise (aggressors).

Figure 7:
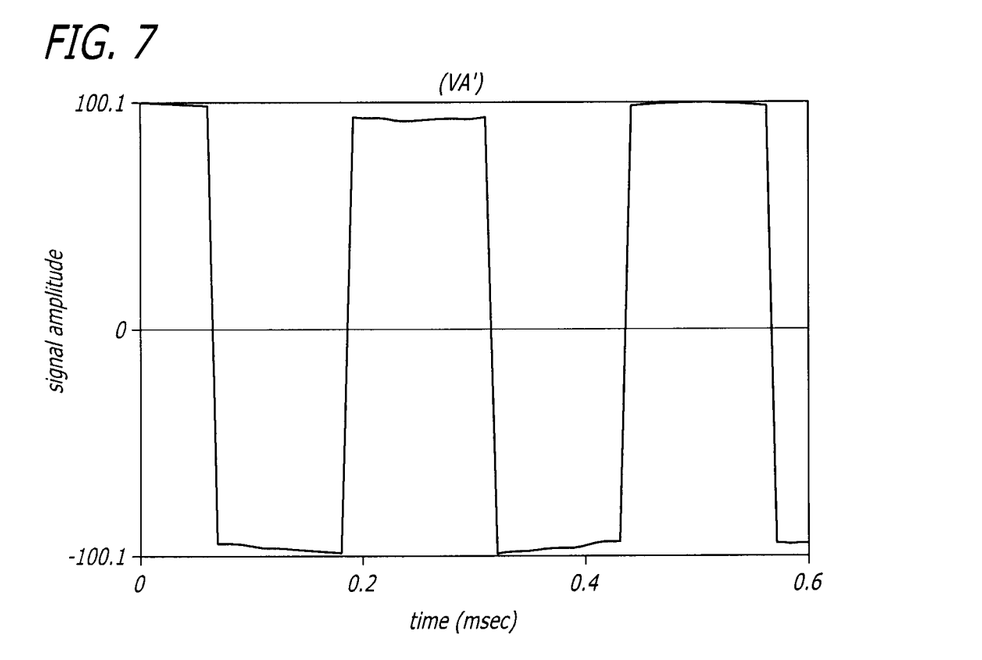
FIG. 7 is a graphical representation of outputted modulated signal VA' in the time domain in accordance with at least one embodiment of the present disclosure.

FIG. 7 shows a graphical representation of outputted modulated signal VA' in the time domain in accordance with at least one embodiment of the present disclosure. This figure shows the resultant amplified signal, which is the outputted modulated signal VA'.

Figure 8:
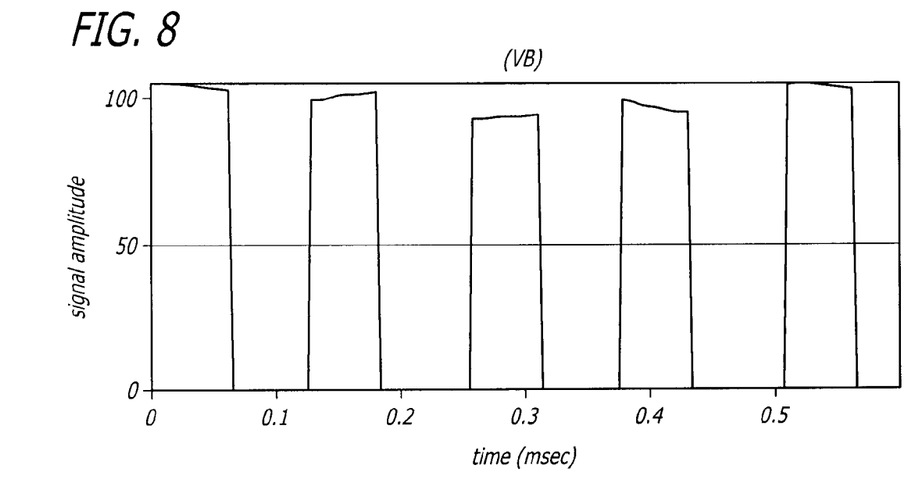
FIG. 8 is a graphical representation of outputted modulated signal VB in the time domain in accordance with at least one embodiment of the present disclosure.

FIG. 8 contains a graphical representation of outputted modulated signal VB in the time domain in accordance with at least one embodiment of the present disclosure. In this figure, the resultant demodulated signal, outputted modulated signal VB, is depicted.

Figure 9:
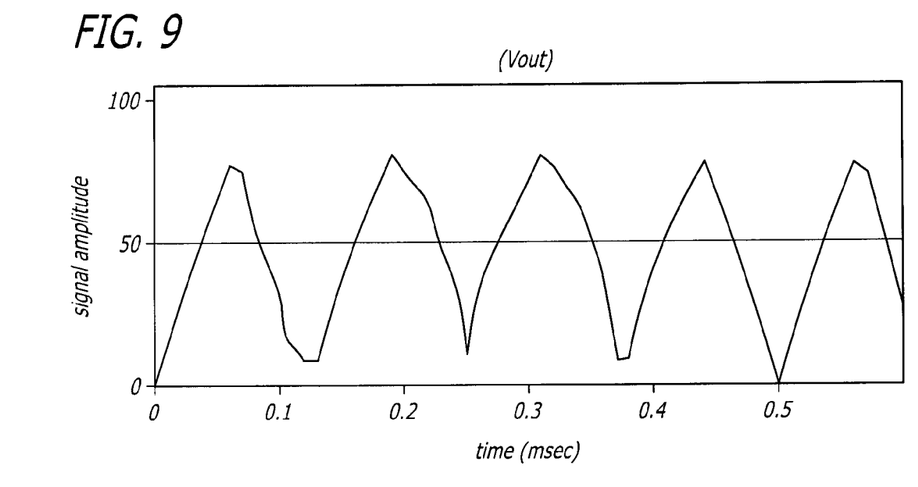
FIG. 9 is a graphical representation of outputted modulated signal Vout in the time domain in accordance with at least one embodiment of the present disclosure.

FIG. 9 illustrates a graphical representation of outputted modulated signal Vout in the time domain in accordance with at least one embodiment of the present disclosure. This figure shows the resultant signal, outputted modulated signal Vout, after it has passed through an integrator.

Figure 10:
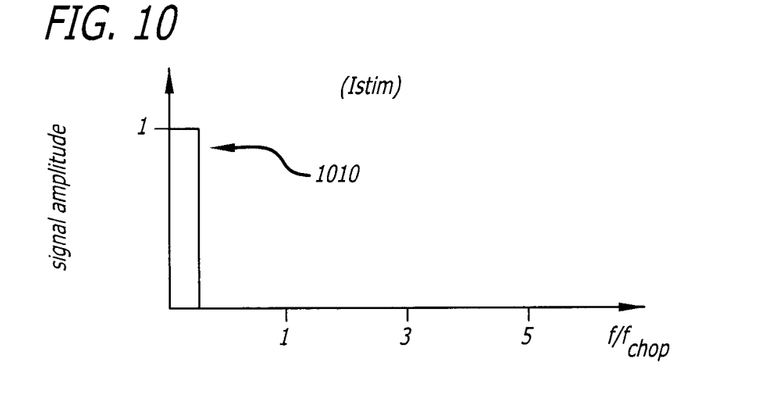
FIG. 10 is a graphical representation of the stimulation current (Istim) in the frequency domain in accordance with at least one embodiment of the present disclosure.

FIG. 10 contains a graphical representation of the stimulation current (Istim) in the frequency domain in accordance with at least one embodiment of the present disclosure. In this figure, the stimulation current (Istim) signal 1010 is shown.

Figure 11:
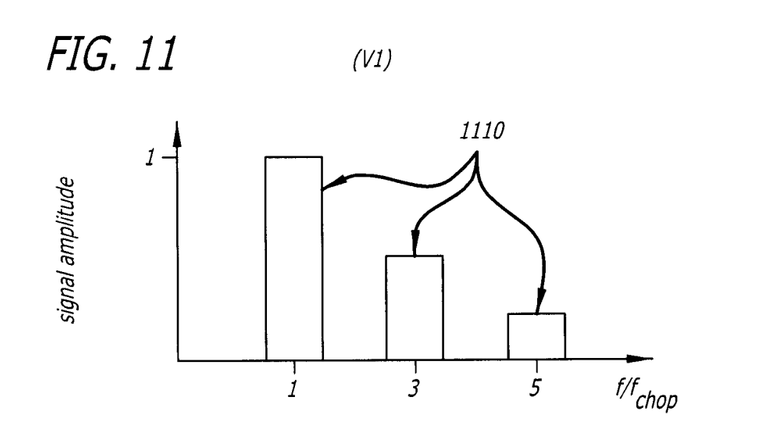
FIG. 11 is a graphical representation of modulated signal V1 in the frequency domain in accordance with at least one embodiment of the present disclosure.

FIG. 11 shows a graphical representation of modulated signal V1 in the frequency domain in accordance with at least one embodiment of the present disclosure. In this figure, the signal of interest 1110 of modulated signal V1 has been modulated to a carrier frequency, "fchop". This frequency is chosen to be outside the bandwidth of typical aggressors, which include environmental noise.

Figure 12:
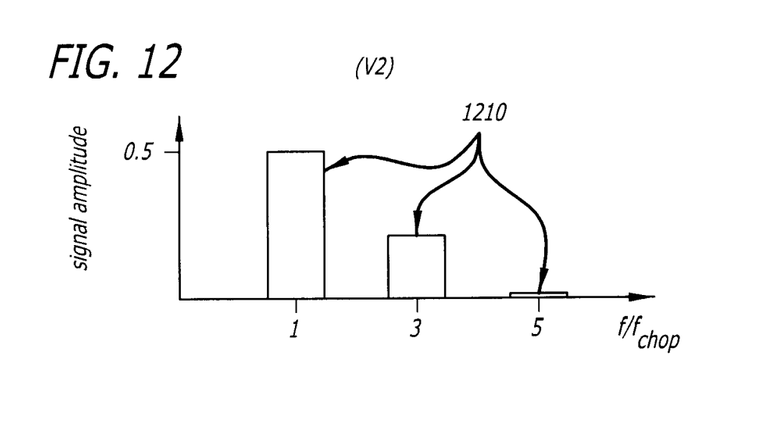
FIG. 12 is a graphical representation of outputted modulated signal V2 in the frequency domain in accordance with at least one embodiment of the present disclosure.

FIG. 12 is a graphical representation of outputted modulated signal V2 in the frequency domain in accordance with at least one embodiment of the present disclosure. In this figure, it is evident that the modulated signal of interest 1210 of outputted modulated signal V2 has a lower signal amplitude than the modulated signal of interest 1110 of modulated signal V1, which is depicted in FIG. 11.

Figure 13:
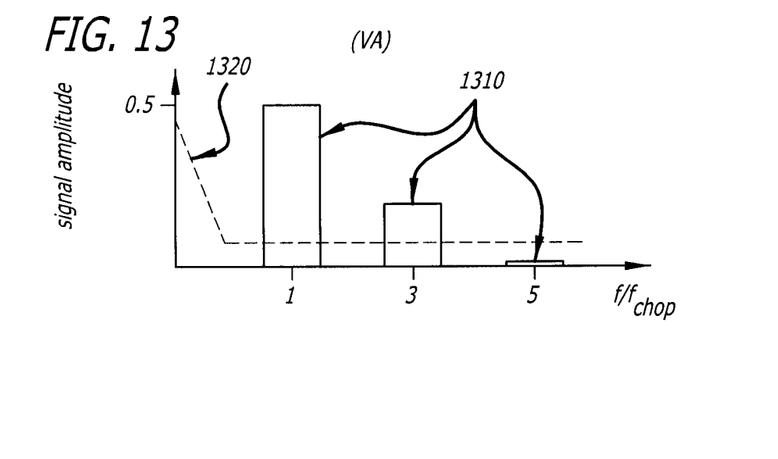
FIG. 13 is a graphical representation of outputted modulated signal VA in the frequency domain in accordance with at least one embodiment of the present disclosure.

FIG. 13 contains a graphical representation of outputted modulated signal VA in the frequency domain in accordance with at least one embodiment of the present disclosure. This figure shows the inclusion of aggressors 1320 with the modulated signal of interest 1310 in outputted modulated signal VA.

Figure 14:
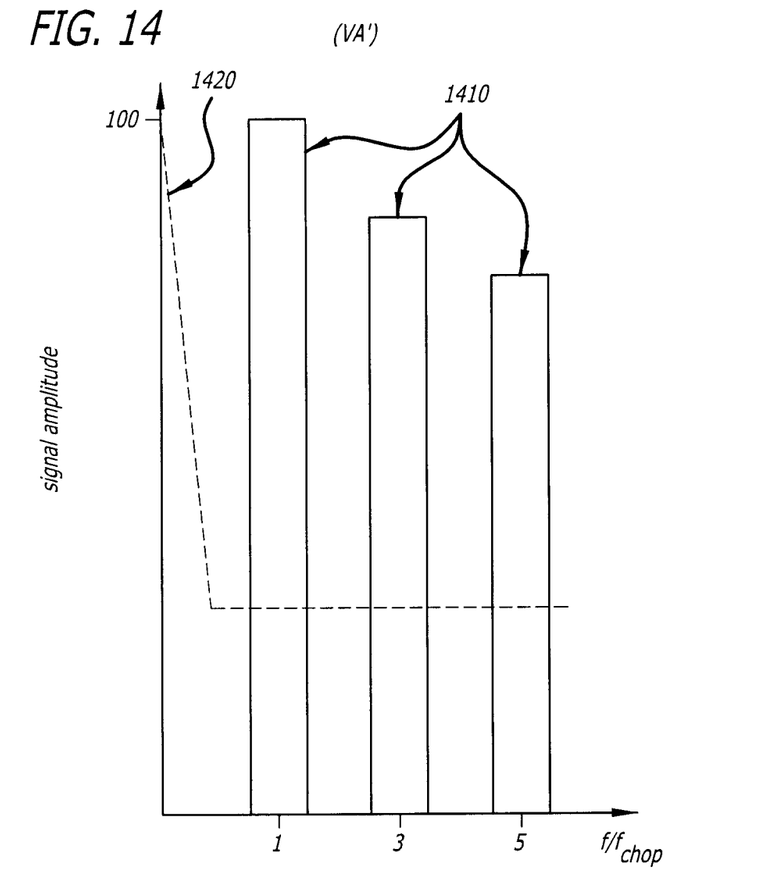
FIG. 14 is a graphical representation of outputted modulated signal VA' in the frequency domain in accordance with at least one embodiment of the present disclosure.

FIG. 14 shows a graphical representation of outputted modulated signal VA' in the frequency domain in accordance with at least one embodiment of the present disclosure. In this figure, it is shown that the outputted modulated signal VA' has a modulated signal of interest 1410 that is amplified at a higher frequency than the aggressors 1420.

Figure 15:
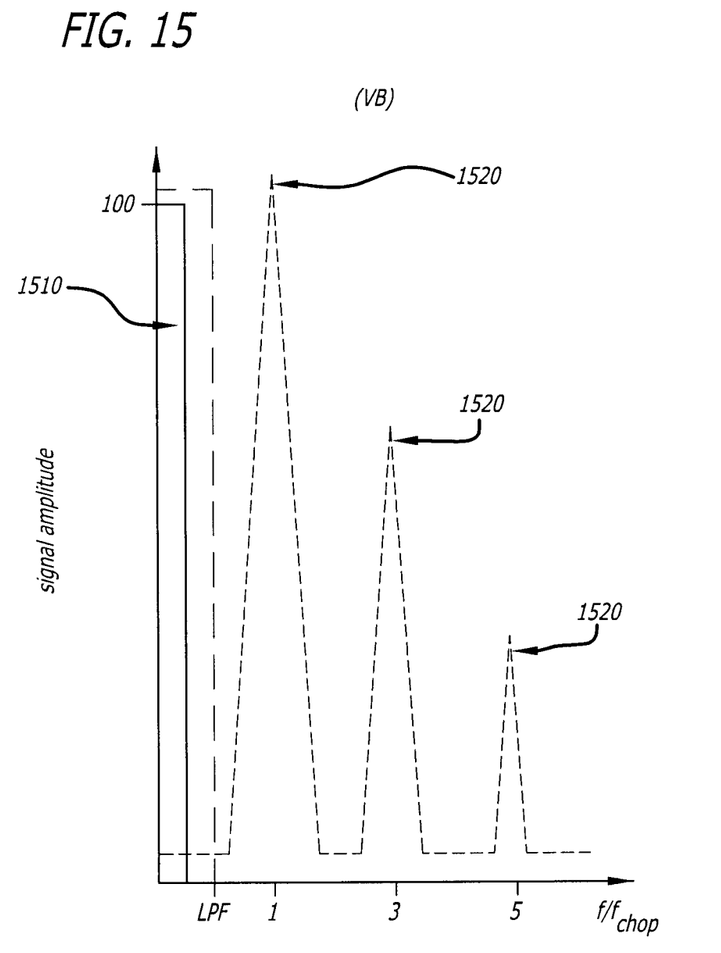
FIG. 15 is a graphical representation of outputted modulated signal VB in the frequency domain in accordance with at least one embodiment of the present disclosure.

FIG. 15 illustrates a graphical representation of outputted modulated signal VB in the frequency domain in accordance with at least one embodiment of the present disclosure. This figure shows that outputted modulated signal VB has a signal of interest 1510 that is demodulated to a lower frequency and has aggressors 1520 that are modulated to a higher frequency. This figure also depicts the low pass filter of the integrator that outputted modulated signal VB will be passed through to produce outputted modulated signal Vout.

Figure 16:
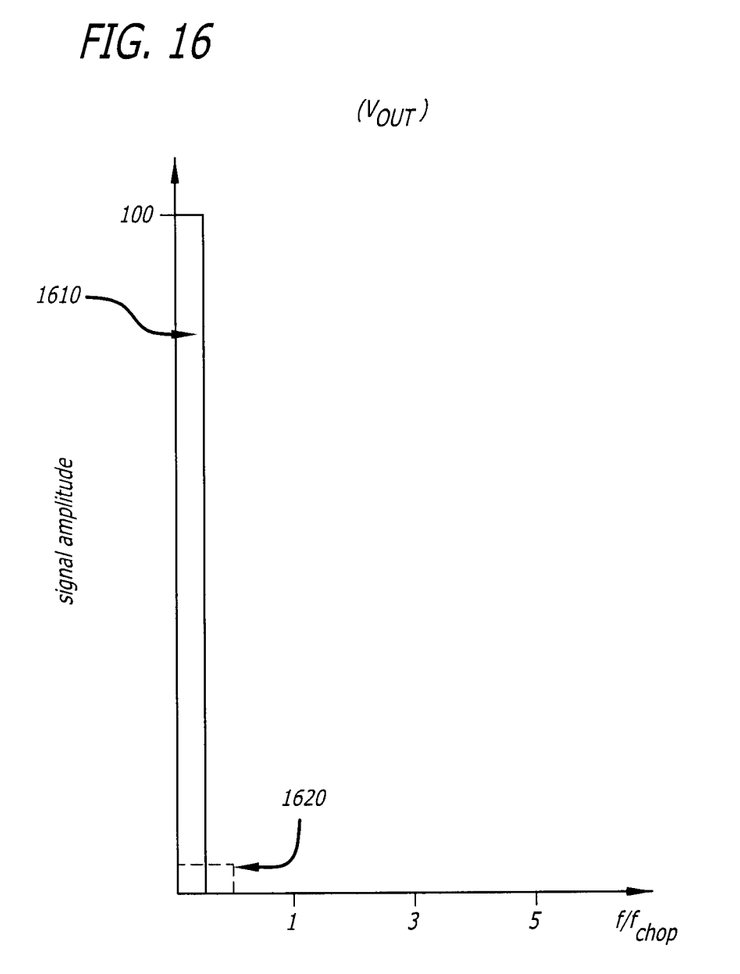
FIG. 16 is a graphical representation of outputted modulated signal Vout in the frequency domain in accordance with at least one embodiment of the present disclosure.

FIG. 16 is a graphical representation of outputted modulated signal Vout in the frequency domain in accordance with at least one embodiment of the present disclosure. In this figure, it is shown that the outputted modulated signal Vout has a signal of interest 1610 that is retained and aggressors 1620 that have been filtered out by an integrator acting as a low pass filter.

Although certain illustrative embodiments and methods have been disclosed herein, it can be apparent from the foregoing disclosure to those skilled in the art that variations and modifications of such embodiments and methods can be made without departing from the true spirit and scope of the art disclosed. Many other examples of the art disclosed exist, each differing from others in matters of detail only. Accordingly, it is intended that the art disclosed shall be limited only to the extent required by the appended claims and the rules and principles of applicable law.

We claim:

1. A method comprising:
    propagating a modulated signal across a myocardium;
    detecting an outputted modulated signal from the myocardium;
    using at least one circuit to reduce the influence of process noise in the outputted modulated signal, wherein the at least one circuit reduces the influence of process noise by at least:
        amplifying the outputted modulated signal to produce a second outputted modulated signal;
        demodulating the second outputted modulated signal to produce a third outputted modulated signal; and
        passing the third outputted modulated signal through an integrator to produce a fourth outputted modulated signal;
    determining an amplitude and phase of the fourth outputted modulated signal, the amplitude and the phase indicating a complex impedance of the myocardium;
    monitoring the indication of complex impedance for complex impedance patterns of the myocardium; and
    based on changes in complex impedance patterns of the myocardium, providing an indication of cardiac function, wherein the cardiac function is at least one of contractility, capture detection, atrium-ventricle optimization, right ventricular function, left ventricular function, cardiac output, or right to left ventricular synchronization.

2. The method of claim 1, wherein the method further comprises:
    providing a direct current signal, wherein the direct current signal is adjustable; and
    modulating the adjustable direct current signal to produce the modulated signal.

3. The method of claim 2, wherein the modulated signal has a nominal frequency of approximately 4 kilohertz to prevent interference with functions of other implanted devices.

4. The method of claim 2, wherein the method further comprises:
    providing an indication of an ischemic event based on changes in complex impedance patterns of the myocardium;
    generating a signal when the ischemic event is indicated, wherein the signal contains an alert message; and
    transmitting the signal.

5. The method of claim 2, wherein the method is employed with at least one implantable medical device (IMD).

6. The method of claim 5, wherein the at least one implantable medical device (IMD) is a cardiac pacemaker.

7. The method of claim 5, wherein the at least one implantable medical device (IMD) is an implantable cardioverter defibrillator (ICD).

8. A system comprising:
at least one electrode configured to propagate a modulated signal across a myocardium;
at least one sensor configured to detect an outputted modulated signal from the myocardium;
at least one circuit configured to reduce the influence of process noise in the outputted modulated signal, wherein the at least one circuit comprises:
an amplifier configured to amplify the outputted modulated signal to produce a second outputted modulated signal;
a demodulator configured to demodulate the second outputted modulated signal to produce a third outputted modulated signal; and
an integrator configured to pass the third outputted modulated signal through to produce a fourth outputted modulated signal; and
at least one processor configured to;
determine an amplitude and phase of the fourth outputted modulated signal, the amplitude and the phase indicating a complex impedance of the myocardium,
monitor the indication of complex impedance for complex impedance patterns of the myocardium, and
based on changes in complex impedance patterns of the myocardium, provide an indication of cardiac function, wherein the cardiac function is at least one of contractility, capture detection, atrium-ventricle optimization, right ventricular function, left ventricular function, cardiac output, or right to left ventricular synchronization.

9. The system of claim 8, wherein the system further comprises a signal generator configured to provide a direct current signal,
wherein the direct current signal is adjustable; and
a modulator configured to modulate the adjustable direct current signal to produce the modulated signal.

10. The system of claim 9, where the modulated signal has a nominal frequency of approximately 4 kilohertz to prevent interference with functions of other implanted devices.

11. The system of claim 9, wherein the system further comprises:
a signal generator configured to generate a signal when an ischemic event is indicated based on changes in complex impedance patterns of the myocardium, wherein the signal contains an alert message; and
a transmitter configured to insert the signal.

12. The system of claim 9, wherein the system further comprises at least one implantable medical device (IMD).

13. The system of claim 12, wherein the at least one implantable medical device (IMD) is a cardiac pacemaker.

14. The system of claim 12, wherein the at least one implantable medical device (IMD) is an implantable cardioverter defibrillator (ICD).

15. A system comprising:
at least one electrode means for propagating a modulated signal across a myocardium;
at least one sensor means for detecting an outputted modulated signal from the myocardium;
at least one circuit means for reducing the influence of process noise in the outputted modulated signal, wherein the at least one circuit means comprises:
an amplifier means for amplifying the outputted modulated signal to produce a second outputted modulated signal;
a demodulator means for demodulating the second outputted modulated signal to produce a third outputted modulated signal; and
an integrator means for passing the third outputted modulated signal through to produce a fourth outputted modulated signal; and
at least one processor means for:
determining an amplitude and phase of the fourth outputted modulated signal, the amplitude and phase indicate a complex impedance of the myocardium,
monitoring the indication of complex impedance for complex impedance patterns of the myocardium, and
based on changes in complex impedance patterns of the myocardium, providing an indication of cardiac function and providing an indication of an ischemic event, wherein the cardiac function is at least one of contractility, capture detection, atrium-ventricle optimization, right ventricular function, left ventricular function, cardiac output, or right to left ventricular synchronization.

16. The system of claim 15, wherein the system further comprises means for providing a direct current signal,
wherein the direct current signal is adjustable; and
means for modulating the adjustable direct current signal to produce the modulated signal.

17. The system of claim 16, wherein the modulated signal has a nominal frequency of approximately 4 kilohertz to prevent interference with functions of other implanted devices.

18. The system of claim 16, wherein the system further comprises:
a signal generator means for generating a signal when the ischemic event is indicated, wherein the signal contains an alert message; and
a transmitter means for transmitting the signal.

19. The system of claim 16, wherein the system further comprises at least one implantable medical device (IMD).

20. The system of claim 19, wherein the at least one implantable medical device (IMD) is a cardiac pacemaker.

21. The method of claim 1, further comprising detecting a plurality of outputted modulated signals collected by a plurality of correlated sensors, and providing an indication of at least one cardiac function based on changes in a plurality of complex impedances, the indication providing information regarding a specific region of the heart.

22. The method of claim 1, wherein the cardiac function is cardiac contractility.

23. A method comprising:
propagating a modulated signal across a myocardium;
detecting an outputted modulated signal from the myocardium;
using at least one circuit to reduce the influence of process noise in the outputted modulated signal, wherein the at least one circuit reduces the influence of process noise by at least:
amplifying the outputted modulated signal to produce a second outputted modulated signal;
demodulating the second outputted modulated signal to produce a third outputted modulated signal; and passing the third outputted modulated signal through an integrator to produce a fourth outputted modulated signal;

determining an amplitude and phase of the fourth outputted modulated signal, the amplitude and the phase indicating a complex impedance of the myocardium;

monitoring the indication of complex impedance for complex impedance patterns of the myocardium; and based on changes in complex impedance patterns of the myocardium, providing an indication of an ischemic event and, determining an area of the ischemic event based on a location of propagation of the modulated signal across the myocardium.

24. The method of claim 23, further comprising:

determining the location of propagation based on changes in patterns sensed by a combination of correlated sensors for specific regions of the heart, and providing an indication of the area of the ischemic event.

25. The system of claim 9, wherein the at least one electrode is a left ventricular tip (LVTIP) electrode, and wherein the at least one sensor is a right ventricular coil (RVCOIL) sensor.

26. The system of claim 9, wherein the at least one electrode is a left ventricular tip (LVTIP) electrode, and wherein the at least one sensor is a right ventricular ring (RVRING) sensor.

27. The system of claim 9, wherein the at least one electrode is a right ventricular tip (RVTIP) electrode, and wherein the at least one sensor is a right ventricular ring (RVRING) sensor.

28. The system of claim 9, wherein the at least one electrode is a left ventricular tip (LVTIP) electrode, and wherein the at least one sensor is a left superior vena cava coil (SVCCOIL) sensor.

29. The system of claim 9, wherein the at least one electrode is a right ventricular tip (RVTIP) electrode, and wherein the at least one sensor is a superior vena cava coil (SVCCOIL) sensor.

* * * * *